US006767342B1

(12) United States Patent
Cantwell

(10) Patent No.: US 6,767,342 B1
(45) Date of Patent: Jul. 27, 2004

(54) OXYGEN BANDAGE SYSTEM

(76) Inventor: Evelyna D. Cantwell, 340 Sunset Dr., Apartment 1405, Ft. Lauderdale, FL (US) 33301

( * ) Notice: Subject to any disclaimer, the term of this patent is extended or adjusted under 35 U.S.C. 154(b) by 119 days.

(21) Appl. No.: 10/127,944

(22) Filed: Apr. 23, 2002

Related U.S. Application Data

(60) Provisional application No. 60/285,451, filed on Apr. 23, 2001.

(51) Int. Cl.[7] .......................... A61F 13/00; A61L 15/16
(52) U.S. Cl. .......................... 604/304; 424/447; 602/48
(58) Field of Search ............................... 424/445, 447; 604/34; 602/48; 428/321.5

(56) References Cited

U.S. PATENT DOCUMENTS

| | | |
|---|---|---|
| 4,801,291 A | 1/1989 | Loori |
| 4,909,244 A | 3/1990 | Quarfoot et al. |
| 5,106,629 A | 4/1992 | Cartmell et al. |
| 5,128,137 A | 7/1992 | Muller et al. |
| 5,154,697 A | 10/1992 | Loori |
| 5,792,090 A | 8/1998 | Ladin |
| 5,855,570 A * | 1/1999 | Scherson et al. ........... 604/304 |
| 6,000,403 A | 12/1999 | Cantwell |
| 6,485,736 B1 * | 11/2002 | Shirley et al. .............. 424/424 |

FOREIGN PATENT DOCUMENTS

| | | |
|---|---|---|
| GB | 2 024 012 | 1/1980 |
| WO | WO 94/21232 | 9/1994 |

* cited by examiner

Primary Examiner—John J. Calvert
Assistant Examiner—Linh Truong
(74) Attorney, Agent, or Firm—Norman E. Lehrer

(57) ABSTRACT

An oxygen bandage system which includes a bandage with first and second sterile pads attached to a covering with an adhesive backing secured thereto is disclosed. Pressure sensitive capsules containing hydrogen peroxide are embedded within the first pad. Covering the first pad is the second pad which has a bottom, wound contacting side and a top side which contacts the first pad. Secured to the top side of the second pad is a film containing potassium manganate. A release liner covers the pads and adhesive backing. In order to use the bandage, the release liner is removed. The bottom side of the second pad is placed over the wound and the adhesive backing is secured to the person's skin surrounding the wound. The hydrogen peroxide is released from the capsule by applying pressure thereto. The first pad contacts the film, thereby activating the film and releasing oxygen to the wound.

6 Claims, 2 Drawing Sheets

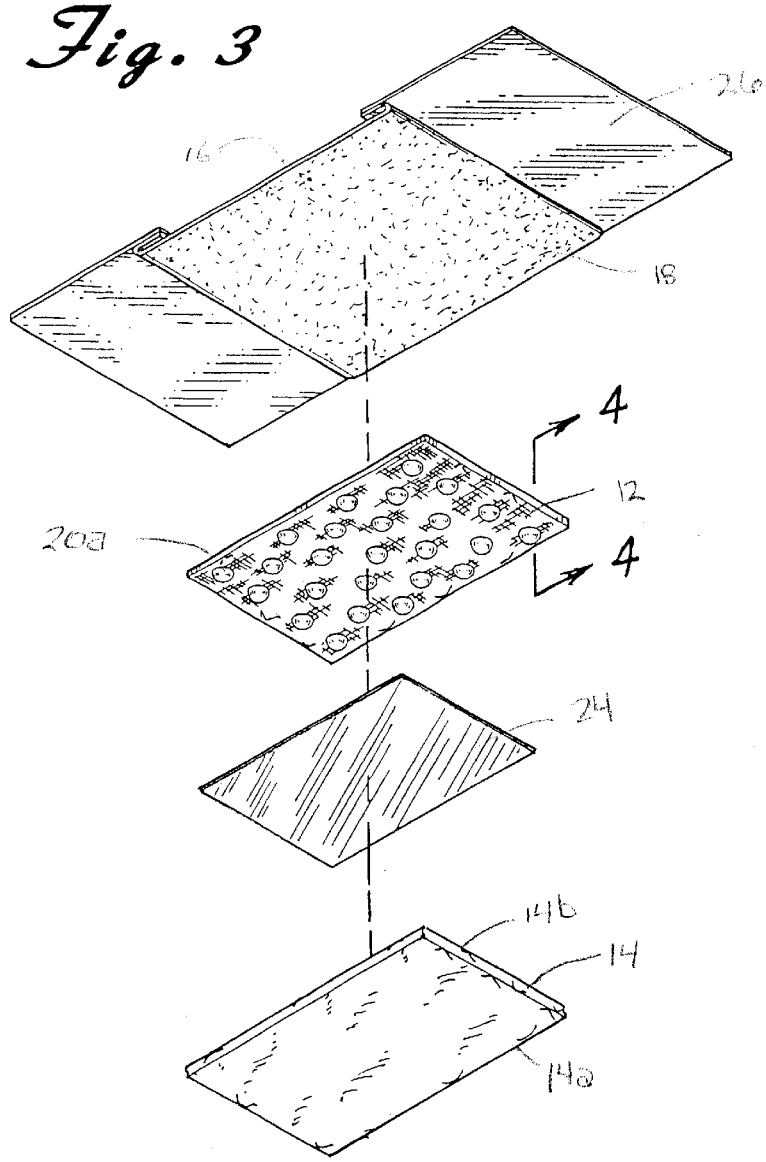
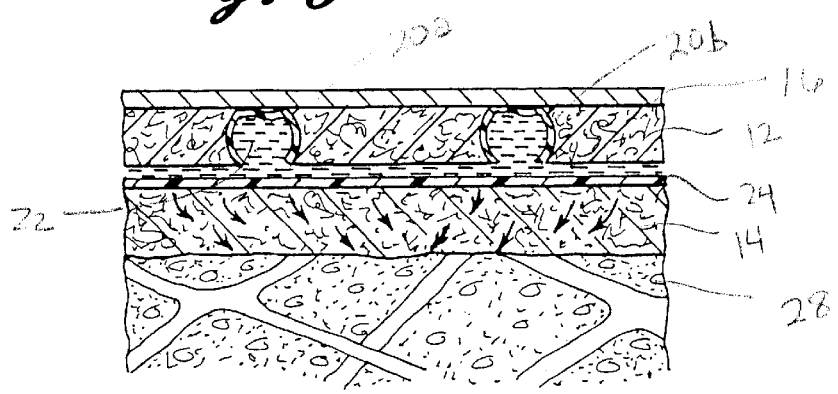

OXYGEN BANDAGE SYSTEM

CROSS-REFERENCE TO RELATED APPLICATION

This application claims the benefit of U.S. Provisional Patent Application Serial No. 60/285,451, filed Apr. 23, 2001.

BACKGROUND OF THE INVENTION

The present invention is directed toward a bandage system and more particularly, toward a bandage which protects a wound yet also supplies oxygen to the wound.

Hyperbaric apparatus for the treatment of open wounds and lesions by applying a therapeutic gas such as oxygen thereto is generally known. See, for example, U.S. Pat. Nos. 5,154,697 and 4,801,291 to Loori. These patents describe various arrangements for the treatment of open lesions in wounds in a hyperbaric chamber with oxygen. This treatment promotes granulation, raises capillary blood oxygen levels, and elevates redox potential thereby suppressing bacterial growth and encouraging revascularization.

In Applicant's prior Patent Application WO94/21323, a topical hyperbaric bandage comprising a gas diffusion resistant flexible and/or resilient sheet material which includes an adhesive layer to be fixed to the skin is disclosed. The adhesive layer surrounds the treatment area. A release layer is disposed over the adhesive layer and means for supplying a therapeutic gas to the treatment area. The device is adapted to retain a single charge of a therapeutic gas over a treatment period.

Heretofore, the containment of oxygen with the exclusion of air has been difficult and has only been practicable in hospitals. However, the advantage of the arrangements discussed above is that they all allow for hyperbaric treatment at home. Yet, these devices are not all self-contained systems.

Hyperbaric oxygen treatment has been somewhat controversial in the past because of the problems with oxygen toxaemia. It has been found that relatively small superatmospheric pressures are effective to assist in revascularization as long as the treatment does not go on for too long. For example, treatments of many conditions for longer than four hours at one time may induce oxygen toxaemia and hence be counterproductive. The practice of flowing oxygen over a lesion for an indeterminate period was not only unnecessary, but clinically counterproductive.

Patent Application No. GB-A-2024012 discloses a two-part storable topical hyperbaric wound dressing which comprises a peroxy compound such as hydrogen peroxide and an agent for activating the hydrogen peroxide in order to produce oxygen. Both components are absorbed or disposed on juxtaposed sheets and rely on either moisture from the wound to achieve activation or from the crushing of microspheres of the initiator prior to assembly about the wound. The problem with this device is that the peroxy compounds are labile when not liquid. Although they may be absorbed on a particular material experimentally, storage in commercial conditions results in the peroxy compound deteriorating rapidly. This is particularly so at higher temperatures.

In Applicant's prior U.S. Pat. No. 6,000,403, a topical hyperbaric bandage comprising a reservoir for a source of therapeutic gas in liquid form is disclosed. Release of the gas from the reservoir is initiated after the bandage has been secured to the skin. This device is a further improvement over the prior art in that it is ready to use, easy to store, and is reliable.

A need still exists, however, for a device which is self-contained, comfortable, sterile, easy to use, and may be self-administered.

SUMMARY OF THE INVENTION

The present invention is designed to overcome the deficiencies of the prior art discussed above. It is an object of the present invention to provide a bandage which protects a wound yet allows oxygen to be introduced to the wound in order to treat it.

It is another object of the present invention to provide a self generating oxygen and containment system which can be used to bathe wounds with oxygen in most parts of the body.

It is yet another object of the present invention to provide a bandage which provides oxygen to a wound and can be self-administered.

It is a further object of the present invention to provide a bandage which is sterile and disposable.

In accordance with the illustrative embodiments demonstrating features and advantages of the present invention, there is provided a bandage with first and second sterile pads attached to a covering with an adhesive backing secured thereto. Pressure sensitive capsules containing hydrogen peroxide are embedded within the first pad. Covering the first pad and secured thereto is the second pad which has a bottom, wound contacting side and a top side which contacts the first pad. Secured to the top side of the second pad is a film containing potassium manganate. A release liner covers the pads and adhesive backing. In order to use the bandage, the release liner is removed. The bottom side of the second pad is placed over the wound and the adhesive backing is secured to the person's skin surrounding the wound. The hydrogen peroxide is released from the capsule by applying pressure thereto so that the hydrogen peroxide saturates the first pad. The first pad which is now wet is in contact with the second pad and film. The potassium permanganate is a catalyst which causes the release of oxygen from the hydrogen peroxide. Oxygen is now released to the wound.

Other objects, features, and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

FIG. 3 is an exploded view of the bandage system of the present invention;

FIG. 6 is a partial cross-sectional view of the bandage system of the present invention when it is activated.

DETAILED DESCRIPTION OF THE PREFERRED EMBODIMENT

Figure 1:
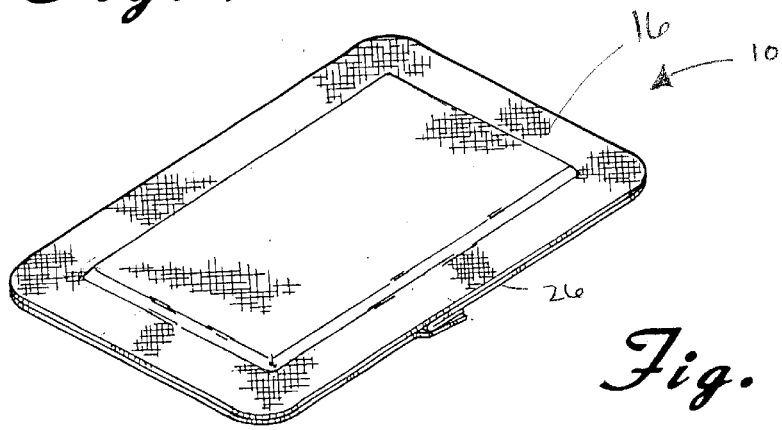
FIG. 1 is a top perspective view of the bandage system of the present invention.
Figure 2:
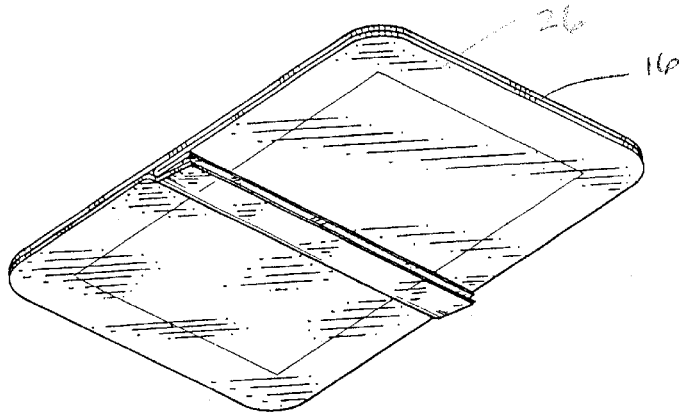
FIG. 2 is a bottom perspective view of the bandage system of the present invention.

Referring now to the drawings in detail wherein like reference numerals have been used throughout the various figures to designate like elements, there is shown in FIG. 1 an oxygen bandage system constructed in accordance with the principles of the present invention and designated generally as 10.

The oxygen bandage system essentially includes a bandage or dressing with a first sterile pad 12 and a second sterile pad 14. The pads 12 and 14 are attached to a covering 16 with an adhesive backing 18 secured to the covering 16. The pads 12 and 14 may be made from cotton gauze or like material generally known and used in the art. The covering may be made from a biocompatible material typically used in the art.

Figure 4:
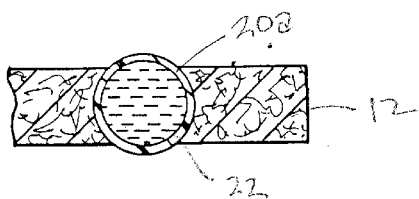
FIG. 4 is a cross-sectional view taken through line 4—4 of FIG. 3.
Figure 5:
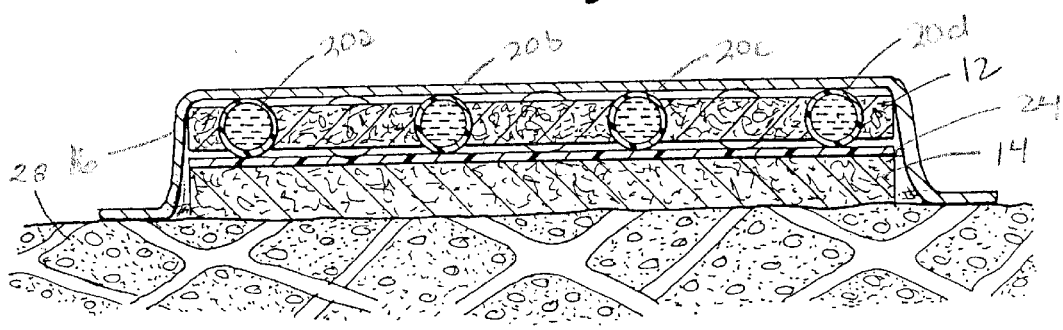
FIG. 5 is a cross-sectional view of the bandage system of the present invention applied to a person's skin.

Pressure sensitive capsules 20a–20d, for example, containing hydrogen peroxide 22 are embedded within the first pad 12. (See FIGS. 4 and 5.) The second pad 14, which is slightly larger than the pad 12, has a bottom, wound contacting side 14a and a top side 14b which contacts the first pad 12 and is secured to the adhesive 18, thereby covering the first pad 12. Secured to the top side 14b of the second pad 14 is a film 24 containing potassium manganate. Alternatively, the film may be embedded within the second pad. Even further, particles of potassium manganate rather than a film may be embedded in either pad. A release liner 26 covers the pads 12 and 14 and adhesive backing 18.

In order to use the bandage, the release liner 26 is first removed. The bottom side 14a of the second pad 14 is then placed over the wound and the adhesive backing 18 is secured to the person's skin 28 surrounding the wound. The hydrogen peroxide 22 is released from the capsules 20a–20d by applying pressure thereto. (See FIG. 6.) For example, the person using the bandage may squeeze the capsules using his or her fingers. The hydrogen peroxide 22 then saturates the first pad 12. The first pad 12 is now wet and is in contact with the second pad 14 and film 24. The potassium manganate film 24 acts as a catalyst to cause the release of oxygen from the hydrogen peroxide. The oxygen moves through the second pad 14 and contacts the wound.

In another embodiment, the hydrogen peroxide may be contained in a layer of gel with a release liner covering the gel. In order to allow the potassium manganate film to act as a catalyst, the release liner is removed so that the gel comes into contact with the film.

The system of the present invention provides a method for introducing oxygen formed in situ to a wound, burn, or injury. Some of the benefits of oxygen action on the body tissues includes, for example, preventing ingress of contamination, discouraging the growth of anaerobic organisms, regranulation of tissue, reducing tissue edema, and stabilizing wounds.

Some of the wounds upon which the present invention may be used include, for example, bedsores, arterial venous ulcers, diabetic wounds, radiation burns, full and split thickness grafts, recluse spider bites, ulcerated shingles, narcotizing fascites, abrasions, cuts, and non-healing post surgical wounds.

The bandage of the present invention can be ergonomically shaped and sized so that it may be used on any part of the body, for example, fingers, hands, arms, neck, face, feet, legs, upper torso, or lower torso. The bandage can be self-administered and used once. Furthermore, the device may be used by the military, outpatients, hospitals, paramedics, or in first aid kits.

Another advantage of the present invention is that oxygen is delivered topically to a wound at low pressures which helps to bathe the wound in oxygen, thereby eliminating flow through turbulence. Also, there is no systemic absorption of oxygen, thus eliminating risk of pulmonary or central nervous system toxicity. Furthermore, because the chemical reaction produces oxygen only at time of use and in measured quantity the product is safe to ship, store, and use.

The present invention may be embodied in other specific forms without departing from the spirit or essential attributes thereof and accordingly, reference should be made to the appended claims rather than to the foregoing specification as indicating the scope of the invention.

I claim:

1. An oxygen bandage system for a wound comprising:
    a bandage having a covering, a first pad, a second pad, and an adhesive backing secured to said covering, said first and second pads attached to said covering;
    an encapsulated liquid containing oxygen located within said bandage; and
    a catalyst located within said bandage, said catalyst being capable of releasing oxygen from said liquid when said liquid is released.

2. The oxygen bandage system for a wound of claim 1 wherein said liquid is hydrogen peroxide.

3. The oxygen bandage system for a wound of claim 1 wherein said catalyst is potassium manganate.

4. The oxygen bandage system for a wound of claim 1 wherein said liquid is encapsulated in pressure sensitive capsules embedded within said first pad.

5. The oxygen bandage system for a wound of claim 4 wherein said catalyst is in the form of a film secured to said second pad.

6. The oxygen bandage system for a wound of claim 5 wherein said second pad has a top side that contacts said first pad and a bottom side that contacts a wound.

* * * * *